(12) United States Patent
Lubock et al.

(10) Patent No.: US 8,292,794 B2
(45) Date of Patent: *Oct. 23, 2012

(54) METHOD FOR MAINTAINING ACCESS TO A BIOPSY SITE

(75) Inventors: Paul Lubock, Laguna Niguel, CA (US); Michael L. Jones, San Clemente, CA (US)

(73) Assignee: Senorx, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/095,304

(22) Filed: Apr. 27, 2011

(65) Prior Publication Data

US 2011/0201966 A1    Aug. 18, 2011

Related U.S. Application Data

(60) Continuation of application No. 11/980,307, filed on Oct. 30, 2007, now Pat. No. 7,955,246, which is a division of application No. 11/357,274, filed on Feb. 17, 2006, which is a continuation-in-part of application No. 11/105,856, filed on Apr. 14, 2005, now Pat. No. 7,214,178, which is a continuation of application No. 10/849,410, filed on May 19, 2004, now Pat. No. 6,955,641, which is a continuation of application No. 10/290,002, filed on Nov. 6, 2002, now Pat. No. 6,923,754.

(51) Int. Cl.
*A61N 5/00* (2006.01)

(52) U.S. Cl. ......................................... 600/3

(58) Field of Classification Search ................. 600/1–8, 600/567
See application file for complete search history.

(56) References Cited

U.S. PATENT DOCUMENTS

| | | | |
|---|---|---|---|
| 3,324,847 A | 6/1967 | Zoumboulis |
| 3,872,856 A | 3/1975 | Clayton |
| 3,975,350 A | 8/1976 | Hudgin et al. |
| 4,119,094 A | 10/1978 | Micklus et al. |
| 4,454,106 A | 6/1984 | Gansow et al. |
| 4,690,677 A | 9/1987 | Erb |
| 4,763,642 A | 8/1988 | Horowitz |

(Continued)

FOREIGN PATENT DOCUMENTS

EP    0536440 A1    4/1993

(Continued)

OTHER PUBLICATIONS

Cuttino, L. W., et al., "CT-Guided Multi-Catheter Insertion Technique for Partial Breast Brachytherapy: Reliable Target Coverage and Dose Homogeneity", Brachytherapy 4, 2005, pp. 10-17, Elsevier.

(Continued)

*Primary Examiner* — Christine Matthews (57) ABSTRACT

A method for maintaining access to a biopsy site within a patient, includes forming a passageway from an opening in an exterior site on the patient to a desired location for a biopsy specimen within the patient; removing a tissue specimen from the desired location thereby leaving a biopsy cavity; providing a temporary catheter having an elongate shaft, a flexible proximal shaft section, and a distal shaft section having a cavity filling member thereon; inserting the cavity filling member on the distal shaft section into the biopsy cavity; inflating the cavity filling member after inserting the cavity filling member within the biopsy cavity, but before closing the opening, using the flexible proximal shaft section; placing the flexible proximal shaft section at an intracorporeal location; and closing the opening so as to seal the passageway.

19 Claims, 4 Drawing Sheets

U.S. PATENT DOCUMENTS

| | | | |
|---|---|---|---|
| 4,929,470 A | 5/1990 | Rittenhouse et al. | |
| 4,998,930 A | 3/1991 | Lundahl | |
| 5,059,166 A | 10/1991 | Fischell et al. | |
| 5,106,360 A | 4/1992 | Ishiwara et al. | |
| 5,167,622 A | 12/1992 | Muto | |
| 5,199,939 A | 4/1993 | Dake et al. | |
| 5,227,969 A | 7/1993 | Waggener et al. | |
| 5,259,847 A | 11/1993 | Trambert | |
| 5,302,168 A | 4/1994 | Hess | |
| 5,312,356 A | 5/1994 | Engelson et al. | |
| 5,314,518 A | 5/1994 | Ito et al. | |
| 5,342,305 A | 8/1994 | Shonk | |
| 5,381,504 A | 1/1995 | Novack et al. | |
| 5,411,466 A | 5/1995 | Hess | |
| 5,417,687 A | 5/1995 | Nardella et al. | |
| 5,428,658 A | 6/1995 | Oettinger et al. | |
| 5,429,582 A | 7/1995 | Williams | |
| 5,503,613 A | 4/1996 | Weinberger | |
| 5,535,817 A | 7/1996 | Dunne | |
| 5,566,221 A | 10/1996 | Smith et al. | |
| 5,603,991 A | 2/1997 | Kupiecki et al. | |
| 5,611,767 A | 3/1997 | Williams | |
| 5,616,114 A | 4/1997 | Thornton et al. | |
| 5,621,780 A | 4/1997 | Smith et al. | |
| 5,653,683 A | 8/1997 | D'Andrea | |
| 5,662,580 A | 9/1997 | Bradshaw et al. | |
| 5,704,926 A | 1/1998 | Sutton | |
| 5,720,717 A | 2/1998 | D'Andrea | |
| 5,759,173 A | 6/1998 | Preissman et al. | |
| 5,782,742 A | 7/1998 | Crocker et al. | |
| 5,820,594 A | 10/1998 | Fontirroche et al. | |
| 5,820,717 A | 10/1998 | Siegenthaler | |
| 5,863,285 A | 1/1999 | Coletti | |
| 5,908,406 A | 6/1999 | Ostapchenko et al. | |
| 5,913,813 A | 6/1999 | Williams et al. | |
| 5,916,143 A | 6/1999 | Apple et al. | |
| 5,919,473 A | 7/1999 | Elkhoury | |
| 5,924,973 A | 7/1999 | Weinberger | |
| 5,931,774 A | 8/1999 | Williams et al. | |
| 5,935,098 A | 8/1999 | Blaisdell et al. | |
| 5,993,972 A | 11/1999 | Reich et al. | |
| 6,022,308 A | 2/2000 | Williams | |
| 6,033,357 A | 3/2000 | Ciezki et al. | |
| 6,036,631 A | 3/2000 | McGrath et al. | |
| 6,083,148 A | 7/2000 | Williams | |
| 6,086,970 A | 7/2000 | Ren | |
| 6,093,142 A | 7/2000 | Ciamacco, Jr. | |
| 6,095,966 A | 8/2000 | Chornenky et al. | |
| 6,143,013 A | 11/2000 | Samson et al. | |
| 6,200,257 B1 | 3/2001 | Winkler | |
| 6,217,565 B1 | 4/2001 | Cohen | |
| 6,251,059 B1 | 6/2001 | Apple et al. | |
| 6,256,529 B1 | 7/2001 | Holupka et al. | |
| 6,282,142 B1 | 8/2001 | Miyawaki | |
| 6,378,137 B1 | 4/2002 | Hassan et al. | |
| 6,390,967 B1 | 5/2002 | Forman et al. | |
| 6,390,968 B1 | 5/2002 | Harmon | |
| 6,390,992 B1 | 5/2002 | Morris et al. | |
| 6,398,708 B1 | 6/2002 | Hastings et al. | |
| 6,413,203 B1 | 7/2002 | Sahatjian | |
| 6,413,204 B1 | 7/2002 | Winkler et al. | |
| 6,416,492 B1 | 7/2002 | Nielson | |
| 6,458,069 B1 | 10/2002 | Tam et al. | |
| 6,482,142 B1 | 11/2002 | Winkler et al. | |
| 6,512,942 B1 | 1/2003 | Burdette et al. | |
| 6,527,693 B2 | 3/2003 | Munro, III et al. | |
| 6,540,655 B1 | 4/2003 | Chin et al. | |
| 6,605,030 B2 | 8/2003 | Weinberger | |
| 6,610,013 B1 | 8/2003 | Fenster et al. | |
| 6,615,070 B2 | 9/2003 | Lee | |
| 6,673,006 B2 | 1/2004 | Winkler | |
| 6,706,014 B2 | 3/2004 | Banik et al. | |
| 6,723,052 B2 | 4/2004 | Mills | |
| 6,746,392 B2 | 6/2004 | Stiger et al. | |
| 6,752,752 B2 | 6/2004 | Geitz | |
| 6,770,058 B1 | 8/2004 | Liprie | |
| 6,913,600 B2 | 7/2005 | Valley et al. | |
| 6,923,754 B2 | 8/2005 | Lubock | |
| 6,983,754 B1 | 1/2006 | Anderson et al. | |
| 7,098,463 B2 | 8/2006 | Adamovics | |
| 7,107,089 B2 | 9/2006 | Lee | |
| 7,171,255 B2 | 1/2007 | Holupka et al. | |
| 7,201,715 B2 | 4/2007 | Burdette et al. | |
| 7,322,929 B2 | 1/2008 | Lovoi | |
| 7,404,791 B2 | 7/2008 | Linares et al. | |
| 7,407,476 B2 | 8/2008 | Lubock et al. | |
| 7,476,235 B2 | 1/2009 | Diederich et al. | |
| 7,497,819 B2 | 3/2009 | White et al. | |
| 7,497,820 B2 | 3/2009 | White et al. | |
| 7,513,861 B2 | 4/2009 | Klein et al. | |
| 7,783,006 B2 | 8/2010 | Stewart et al. | |
| 7,885,382 B2 | 2/2011 | Stewart et al. | |
| 7,887,476 B2 | 2/2011 | Hermann et al. | |
| 7,955,246 B2 * | 6/2011 | Lubock et al. | 600/3 |
| 2001/0049464 A1 | 12/2001 | Ganz | |
| 2001/0051669 A1 | 12/2001 | McGhee | |
| 2002/0045893 A1 | 4/2002 | Lane et al. | |
| 2002/0055666 A1 | 5/2002 | Hunter et al. | |
| 2002/0095114 A1 | 7/2002 | Palasis | |
| 2002/0177804 A1 | 11/2002 | Saab | |
| 2003/0144570 A1 | 7/2003 | Hunter et al. | |
| 2004/0039437 A1 | 2/2004 | Sparer et al. | |
| 2004/0054366 A1 | 3/2004 | Davison et al. | |
| 2004/0116767 A1 | 6/2004 | Lebovic et al. | |
| 2005/0061771 A1 | 3/2005 | Murphy | |
| 2005/0080313 A1 | 4/2005 | Stewart et al. | |
| 2005/0124843 A1 | 6/2005 | Singh | |
| 2005/0240073 A1 | 10/2005 | Apffelstaedt et al. | |
| 2005/0277577 A1 | 12/2005 | Hunter et al. | |
| 2006/0020156 A1 | 1/2006 | Shukla | |
| 2006/0020256 A1 | 1/2006 | Bell et al. | |
| 2006/0100475 A1 | 5/2006 | White et al. | |
| 2006/0116546 A1 | 6/2006 | Eng | |
| 2006/0136051 A1 | 6/2006 | Furst et al. | |
| 2006/0167416 A1 | 7/2006 | Mathis et al. | |
| 2006/0173233 A1 | 8/2006 | Lovoi | |
| 2006/0173235 A1 | 8/2006 | Lim et al. | |
| 2007/0005003 A1 | 1/2007 | Patterson et al. | |
| 2007/0055144 A1 | 3/2007 | Neustadter et al. | |
| 2007/0106108 A1 | 5/2007 | Hermann et al. | |
| 2007/0270627 A1 | 11/2007 | Cutrer et al. | |
| 2008/0057298 A1 | 3/2008 | Finley | |
| 2008/0091055 A1 | 4/2008 | Nguyen et al. | |
| 2008/0221384 A1 | 9/2008 | Chi Sing et al. | |
| 2008/0221444 A1 | 9/2008 | Ritchie et al. | |
| 2008/0228024 A1 | 9/2008 | Jones et al. | |
| 2008/0287801 A1 | 11/2008 | Magnin et al. | |
| 2009/0171157 A1 | 7/2009 | Diederich et al. | |
| 2009/0188098 A1 | 7/2009 | Acosta et al. | |

FOREIGN PATENT DOCUMENTS

| | | |
|---|---|---|
| EP | 0642766 A2 | 3/1995 |
| EP | 0693293 B1 | 1/1996 |
| EP | 0719571 A2 | 7/1996 |
| EP | 0853957 B1 | 7/1998 |
| EP | 0867200 A2 | 9/1998 |
| EP | 1051990 A1 | 11/2000 |
| EP | 1070514 A1 | 1/2001 |
| EP | 1541188 A1 | 6/2005 |
| EP | 1618924 A1 | 1/2006 |
| JP | 10137250 A | 5/1998 |
| JP | 2001120561 A | 5/2001 |
| RU | 2177350 C2 | 12/2001 |
| WO | 9520241 A1 | 7/1995 |
| WO | 9712540 A1 | 4/1997 |
| WO | 9745053 A2 | 12/1997 |
| WO | 9815315 A1 | 4/1998 |
| WO | 9934869 A1 | 7/1999 |
| WO | 0158346 A1 | 8/2001 |
| WO | 0209599 A2 | 2/2002 |
| WO | 02069862 A1 | 9/2002 |
| WO | 2005039655 A1 | 5/2005 |
| WO | 2005039665 A1 | 5/2005 |
| WO | 2005067442 A2 | 7/2005 |
| WO | 2007027831 A1 | 3/2007 |
| WO | 2007143560 A2 | 12/2007 |

OTHER PUBLICATIONS

Glasgow, G. P., et al. "Remote Afterloading Technology", AAPM Report No. 41, 1993, pp. i-vi and 1-107, American Institute of Physics, Inc.

Hoshino, T., "Brain Tumor Research Center", Abstracts of the 11th Conference on Brain Tumor Research and Therapy, Journal of Neuro-Oncology 28, 1996, pp. 31-113.

Paul V. Harper, "Some Therapeutic Applications of Radioisotopes", Journal of the Mississippi State Medical Association, Oct. 1966, vol. VII, pp. 526-533.

"Variable shield for radiation-therapy source wire and centering catheter", Research disclosure, Mason Publications, Hampshire, GB, vol. 438, No. 48, Oct. 2000, XP007126916.

Gregory K. Edmundson, et al., "Dosimetric Characteristics of the Mammosite RTS, a New Breast Brachytherapy Applicator", Int. J. Radiation Oncology Biol. Phys, vol. 52, No. 4, pp. 1132-1139, 2002.

Melvin A. Astrahan, PhD et al., "Optimization of Mammosite therapy", Int. J. Radiation Oncology Biol. Phys, vol. 58, No. 1, pp. 220-232, 2004.

Philip H. Gutin, et al., "A coaxial catheter system for afterloading radioactive sources for the interstitial irradiation of brain tumors", J. Neurosur, vol. 56, pp. 734-735, 1982.

R.D. Ashpole et al., "A New Technique of Brachytherapy for Malignant Gliomas with Caesium-137; A New Method Utilizing a Remote Afterloading system", Clinical Oncology, (1990).

Abstracts of the 11th International Conference on Brain tumor Research and Therapy Oct. 31-Nov. 3, 1995, Silverado Country Club and Resort, Napa, California, Journal of Neuro-Oncology 28:72, 1996.

Johannesen, T.B. et al, "Intracavity Fractioned Balloon Brachytherapy in Glioblastoma", Acta Neurochir (Wien) (1999) 141: 127-133.

Tanderup, et al, "Multi-Channel Intracavitary Vaginal Brachytherapy Using Three-Dimensional Optimization of Source Geometry", Radiation & Oncology Journal of the European Society for Therapeutic Radiology and Oncology, 2004, pp. 81-85, Radiotherapy and Oncology 70 (2004), Elsevier Ireland Ltd.

Devic, et al., "Advantages of Inflatable Multichannel Endorectal Applicator in the Neo-Adjuvant Treatment of Patients With Locally Advanced Rectal Cancer With HDR Brachytherapy", Journal of Applied Clinical Medical Physics, Spring 2005, pp. 44-49, vol. 6, No. 2.

Symon, et al. "Individual Fraction Optimization vs. First Fraction Optimization for Multichannel Applicator Vaginal Cuff High-Dose-Rate Brachytherapy", pp. 211-215, Brachytherapy 5 (2006), Elsevier.

Friedman, M, et al., "A New Technic for the Radium Treatment of Carcinoma of the Bladder", Presented at the Thirty-fourth Annual Meeting of the Radiological Society of North America, Dec. 5-10, 1948, pp. 342-362.

Walton, R. J., "Therapeutic Uses of Radioactive Isotopes in the Royal Cancer Hospital", The British Journal of Radiology, 1950, pp. 559-599, William Heinemann, Publisher.

Low-Beer, B. V. A., "Radioisotope Therapy", "The Clinical Use of Radioactive Isotopes" 1950, pp. 284-349, Charles C. Thomas, Publisher, Springfield, Illinois, U.S.A., See pp. 343-349.

Low-Beer, B. V. A., "The Therapeutic Use of Radioactive Isotopes", "Practical Therapeutics", Dec. 1954, pp. 69-87, vol. X, No. 6.

Muller, J. H., "Radiotherapy of Bladder Cancer by Means of Rubber Balloons Filled In Situ With solutions of a Radioactive Isotope (Co60)", Cancer, A Journal of the American Cancer Society, Jul.-Aug. 1955, pp. 1035-1043, vol. 8, No. 4, J. B. Lippincott Company, Philiadelphia.

Friedman, M, et al., "Irradiation of Carcinoma of the Bladder by a Central Intracavitary Radium or Cobalt 60 Source (The Walter Reed Technique)", Presented at the Annual Meeting of the American Radium Society, 1955, pp. 6-31.

Hewitt, C. B., et al., "Update on Intracavitary Radiation in the Treatment of Bladder Tumors", The Journal of Urology; Official Journal of the American Urological Association, Inc., 1981, pp. 323-325, vol. 126 September, The Williams & Wilkins Co.

Hieshima, G. B., et al. "A Detachable Balloon for Therapeutic Transcatheter Occlusions 1", Technical Notes, Jan. 1981, pp. 227-228, vol. 138.

Russel, A. H., et al, "Intracavitary Irradiation for Carcinoma of the Urinary Bladder: Rationale, Technique, and Preliminary Results", Int. J. Radiation Oncology. Phys,. 1984, pp. 215-219, vol. 10, Pergamon Press Ltd.

Yin, W., "Brachtherapy of Carcinoma of the Esophagus in China, 1970-1974 and 1982-1984", Brachytherapy HDR and LDR, May 4-6, 1989, pp. 52-56.

Kaufman, N., "Remote Afterloading Intraluminal Brachytherapy in the Treatment of Rectal, Rectosigmoid, and Anal Cancer: A Feasibility Study", International Journal of Radiation Oncology, Biology, Physics, Sep. 1989, pp. 663-668, vol. 17, Issue 3, Pergamon Press plc.

Wolf, C. D., et al., "A Unique Nasopharynx Brachytherapy Technique", Official Journal of the American Association of Medical Dosimetrists, 1990, pp. 133-136, vol. 15, Issue No. 3., Pergamon Press.

Fowler, J. F., "Brief Summary of Radiobiological Principles in Fractionated Radiotherapy", Seminars in Radiation Oncology, Jan. 1992, pp. 16-21, vol. 2, No. 1, W. B. Saunders Company.

Nag, S, "Modern Techniques of Radiation Therapy for Endometrial Cancer", Clinical Obstetrics and Gynecology, Sep. 1996, pp. 728-744, vol. 39, No. 3, Lippincott-Raven Publishers.

Pernot, M., "Combined Surgery and Brachytherapy in the Treatment of Some Cancers of the Bladder (Partial Cystectomy and Interstitial Iridium—192)", Radiotherapy & Oncology, 1996, pp. 115-120, Elsevier Science Ireland Ltd.

Micheletti, E., et al., "High-Dose-Rate Brachytherapy for Poor-Prognosis, High-Grade Glioma: (Phase II) Preliminary Results", Tumori, 1996, pp. 339-344.

Nag, S., et al., "Perineal Template Interstitial Barchytherapy Salvage for Recurrent Endometrial Adenocarcinoma Metastatic to the Vagina", Necologic Oncology 66, 1997, pp. 16-19, Article No. GO974722, Academic Press.

Nag, S., et al., "Remote Controlled High Dose Rate BrachytheraBrachytherapy", Critical Reviews in Oncology/Hematology 22, 1996, pp. 127-150, Elsevier Science Ireland Ltd.

Sylvester, J., et al., "Interstitial Implantation Techniques in Prostate Cancer" Journal of Surgical Oncology 1997; 66: 65-75, Wiley-Liss, Inc.

Tan, L. T., et al., Radical Radiotherapy for Carcinoma of the Uterine Cervix Using External Beam Radiotherapy and a Single Line Source Brachytherapy Technique: The Clatterbridge Technique, The British Journal of Radiology, 70, date Dec. 1997, pp. 1252-1258.

Kuettel, M. R., et al., "Treatment of Female Urethral Carcinoma in Medically Inoperable Patients Using External Beam Irradiation and High Dose Rate Intracavitary Brachytherapy" The Journal of Urology, May 1997, pp. 1669-1671, vol. 157, The American Urological Association, Inc.

Slevin, N. J., et al., "Intracavitary Radiotherapy Boosting for Nasopharynx Cancer" The British Journal of Radiology, 70, Apr. 1997, pp. 412-414.

Sneed, P, K., et al., Interstitial Brachytherapy Procedures for Brain Tumors, Seminars in Surgical Oncology 1997; 13: 157-166, Wiley-Liss, Inc.

Dempsey, J. F., et al., "Dosimetric Properties of a Novel Brachytherapy Balloon Applicator for the Treatment of Malignant Brain-Tumor Resection-Cavity Margins" Int. J. Radiation Oncology Biol. Phys., May 1998, pp. 421-429, vol. 42, No. 2, Elsevier.

Kolotas, C., et al., "CT Guided Interstitial High Dose Rate Brachytherapy for Recurrent Malignant Gliomas", The British Journal of Radiology, 72, (1999), pp. 805-808.

Demanes, D, J., et al., "The Use and Advantages of a Multichannel Vaginal Cylinder in High-Dose-Rate Brachytherapy", Int. J. Radiation Oncology Biol. Phys., (1999), pp. 211-219, vol. 44, No. 1, Elsevier Science Inc.

Debicki, M. P., et al., "Localized Current Field Hyperthermia in Carcinoma of the Cervix: 3-D Computer Simulation of SAR Distribution", International Journal of Hyperthermia, 1999, pp. 427-440, vol. 15, No. 5.

Garipagaoglu, M, et al., "Geometric and Dosimetric Variations of ICRU Bladder and Rectum Reference Points in Vaginal Cuff Brachytherapy Using Ovoids", Int. J. Radiation Oncology Biol. Phys.. 2004, pp. 1607-1615, Elsevier Inc.

Bowsher, W. G., et al., "Update on Urology-Prostate Cancer, 4-Treatment of Local Disease", European Journal of Surgical Oncology, 1995 pp. 679-682, vol. 21, No. 6.

Voung, T, et al., "High-Dose-Rate Endorectal Brachytherapy in the Treatment of Loacally Advanced Rectal Carcinoma: Technical Aspects", Brachytherapy 4, 2005, pp. 230-235, Elsevier.

Harada, T, et al., "Transcystoscopic Intracavitary irradiation for Carcinoma of the Bladder: Technique and Preliminary Clinical Results", The Journal of Urology, Oct. 1987, pp. 771-774, vol. 138, No. 4, The Williams & Wilkins Co.

Hall, J. W., et al., "Histologic Changes in Squamous-Cell Carcinoma of the Mouth and Oropharynx Produced by Fractionated External Roentgen Irradiation", Radiological Society of North America, 1948, pp. 318-350, 50/3/MAR.

Hine, G. J., et al., "Isodose Measurements of Linear Radium Sources in Air and Water by Means of an Automatic Isodose Recorder",The American Journal of Roentgenology and Radium Therapy, 1950, pp. 989-998, vol. 64, No. 6, The Societies.

Walton, R. J., et al., Radioactive Solution (24Na and 82 Br) in the Treatment of Carcinoma of the Bladder:, British Medical Bulletin, 1952, pp. 158-165, Medical Dept., The British Council.

Marshall V. F., et al., "Current Clinical Problems Regarding Bladder Tumors", Symposium on Bladder Tumors, 1956, pp. 543-550, 9/3/May-Jun. J. B. Lippincott Co, Etc.

Hewitt, C. B., et al., "Intracavitary Radiation in the Treatment of Bladder Tumors", The Journal of Urology, vol. 107, Apr. 1972, pp. 603-606, The Williams & Wilkins Co.

Rotman, M., et al., "The Intracavitary Applicator in Relation to Complications of Pelvic Radiation-The Ernst System", Int. J. Radiation Oncology Biol. Phys., 1978, pp. 951-956, vol. 4, Pergamon Press Inc.

Nag, S., et al., "The Future of High Dose Rate Brachytherapy", High Dose Rate Brachytherapy: A Textbook, 1994, pp. 447-453, Futura Publishing Company, Inc. , Armonk, New York 10504.

Wang, C. C., "Carcinoma of the Nasopharynx", Radiation Therapy of Head and Neck Neoplasms, 1997, pp. 257-280, Chapter 10, Wiley-Liss, Inc.

Gaspar, L. E., et al., "Esophageal Brachytherapy", Principles and Practice of Brachytherapy, 1997, pp. 305-321, Futrua Publishing Company, Inc., Armouk, New York.

Vicini, F. A., et al, "Dose-Volume Analysis for Quality Assurance of Interstitial Brachytherapy for Breast Cancer", Int. J. Radiation Oncology Biol. Phys., vol. 45, 1999, pp. 803-810, Elsevier Science Inc.

Akagi, Y, et al., "Optimum Fractionation for High-Dose-Rate Endoesophageal Brachytherapy Following External Irradiation of Early State Esophageal Cancer", Int. J. Radiation Oncology Biol. Phys., vol. 43, 1999, pp. 525-530, Elsevier Science, Inc.

Xu, Z., et al., "Calculation of Dose Distribution Near an Innovative Concentric Balloon Catheter for Endovascular Brachytherapy", Cardiovascular Radiation Medicine 2, 2000, pp. 26-31, Elsevier Science Inc.

Stubbs, J. B., et al., "Preclinical Evaluation of a Novel Device for Delivering Brachytherapy to the Margins of Resected Brain Tumor Cavities", J. Neurosurg 96, Feb. 2002, pp. 335-343, vol. 96.

Das, R. K., et al., "3D-CT-Based High-Dose-Rate Breast Brachytherapy Implants: Treatment Planning and Quality Assurance", Int. J. Radiation Oncology Biol. Phys. 2004, pp. 1224-1228, vol. 59, No. 4, Elsevier Inc.

* cited by examiner

METHOD FOR MAINTAINING ACCESS TO A BIOPSY SITE

RELATED APPLICATIONS

This application is a continuation of application 11/980,307 filed Oct. 30, 2007, now U.S. Pat. No. 7,955,246, which is a division of application Ser. No. 11/357,274 filed Feb. 17, 2006, which is a continuation-in-part of application Ser. No. 11/105,856 filed Apr. 14, 2005, now U.S. Pat. No. 7,214,178, which is a continuation of application Ser. No. 10/849,410 filed May 19, 2004, now U.S. Pat. No. 6,955,641, which is a continuation of application Ser. No.10/290,002 filed Nov. 6, 2002, now U.S. Pat. No. 6,923,754. All of these applications are incorporated herein in their entireties by reference.

FIELD OF THE INVENTION

This invention generally relates to medical treatment devices and methods of using such devices. In particular, the invention is directed to devices and methods for temporarily maintaining access to a cavity in a targeted tissue region, such as a biopsy site from which cancerous, pre-cancerous or other tissue has been removed, to provide subsequent treatments to the tissue surrounding the cavity.

BACKGROUND OF THE INVENTION

In diagnosing and treating certain medical conditions, it is often desirable to perform a biopsy, in which a specimen or sample of tissue is removed for pathological examination, tests and analysis. A biopsy typically results in a biopsy cavity occupying the space formerly occupied by the tissue that was removed. As is known, obtaining a tissue sample by biopsy and the subsequent examination are typically employed in the diagnosis of cancers and other malignant tumors, or to confirm that a suspected lesion or tumor is not malignant. Treatment of cancers identified by biopsy may include subsequent removal of tissue surrounding the biopsy site, leaving an enlarged cavity in the patient's body. Cancerous tissue is often treated by application of radiation, by chemotherapy, or by thermal treatment (e.g., local heating, cryogenic therapy, and other treatments to heat, cool, or freeze tissue).

Cancer treatment may be directed to a natural cavity, or to a cavity in a patient's body from which tissue has been removed, typically following removal of cancerous tissue during a biopsy or surgical procedure. For example U.S. Pat. No. 6,923,754 to Lubock and U.S. patent application Ser. No. 10/849,410 to Lubock, describe devices for implantation into a cavity resulting from the removal of cancerous tissue which can be used to deliver cancer treatments to surrounding tissue. One form of radiation treatment used to treat cancer near a body cavity remaining following removal of tissue is "brachytherapy" in which a source of radiation is placed near to the site to be treated.

The Lubock patent and patent application, above, describe implantable devices for treating tissue surrounding a cavity left by surgical removal of cancerous or other tissue that includes a cavity filling member such as an inflatable balloon constructed for placement in the cavity. The Lubock devices develop a vacuum within the biopsy cavity that is effective to draw surrounding tissue close to the surface of a treatment assembly so as to conform the tissue lining the cavity to the surface of the balloon. Such devices may be used to apply one or more of radiation therapy, chemotherapy, and thermal therapy to the tissue surrounding the cavity from which the tissue was removed. The balloon may be filled with a treatment fluid delivered via a conduit from a receptacle, syringe, or other means, or may receive a solid radiation source placed within the balloon.

For example, a "MammoSite® Radiation Therapy System" (MammoSite® RTS, Proxima Therapeutics, Inc., Alpharetta, Ga. 30005 USA) includes a balloon catheter with a radiation source that can be placed within a tumor resection cavity in a breast after a lumpectomy. It can deliver a prescribed dose of radiation from inside the tumor resection cavity to the tissue surrounding the original tumor. Inflatable treatment delivery devices and systems, such as the MammoSite® RTS and similar devices and systems (e.g., GliaSite® RTS (Proxima Therapeutics, Inc.)), are useful to treat cancer in tissue adjacent a body cavity.

Long term deployment of the catheter within the biopsy site may be necessary, e.g. for a few days to a few weeks to maintain access to the biopsy cavity while the biopsy sample is analyzed and it is determined whether or not irradiation of the cavity is necessary. The irradiation is not always necessary for a body cavity formed after removal of tissue. When irradiation is not needed the catheters are removed and disposed of. When in place within the patient, the proximal ends of the prior art catheters extend out of the patient providing direct access for infections to reach the biopsy site.

The prior catheters are expensive and a catheter used only to hold the shape of the biopsy cavity is disposed of afterwards. Thus there is need in the art for less expensive devices which are temporary and capable of maintaining access to the biopsy device with reduced risk of infection.

SUMMARY OF THE INVENTION

The invention is directed to methods and devices for temporary subcutaneous deployment while at least partially filling a body cavity in a targeted tissue region within a patient's body, such as a cavity formed by the removal of tissue from a patient. The catheter device embodying features of the invention has distal shaft section with a cavity filling member such as an inflatable member (e.g. balloon) and the proximal shaft portion of the device is configured to be deployed subcutaneously so that no direct access is provided to the intracorporeal cavity for pathogens.

The invention, in one form thereof, is directed to a method for maintaining access to a biopsy site within a patient. The method includes forming a passageway from an opening in an exterior site on the patient to a desired location for a biopsy specimen within the patient; removing a tissue specimen from the desired location thereby leaving a biopsy cavity; providing a temporary catheter having an elongate shaft, a flexible proximal shaft section, and a distal shaft section having a cavity filling member thereon; inserting the cavity filling member on the distal shaft section into the biopsy cavity; inflating the cavity filling member after inserting the cavity filling member within the biopsy cavity, but before closing the opening, using the flexible proximal shaft section; placing the flexible proximal shaft section at an intracorporeal location; and closing the opening so as to seal the passageway.

The invention, in another form thereof, is directed to a method of temporarily filling an intracorporeal site within a breast of a patient. The method includes forming an opening in the breast; forming a passageway in the breast from the opening in the breast to a desired intracorporeal location; forming a cavity in the breast at the desired intracorporeal location; providing a catheter device having an elongated shaft with a flexible proximal shaft section, a distal shaft section and a cavity filling member on the distal shaft section;

inserting the catheter device through the opening and advancing the catheter device within the passageway until the cavity filling member on the distal shaft section is disposed within the cavity formed in the breast; inflating the cavity filling member after disposing the cavity filling member within the cavity in the breast, but before closing the opening, using the flexible proximal shaft section; placing the flexible proximal shaft section used to inflate the cavity filling member within the breast; and closing the opening after placing the flexible proximal shaft section within the breast.

The invention, in another form thereof, is directed to a method for maintaining access to a body cavity at an intracorporeal location of a patient. The method includes providing a catheter having an elongate shaft, a flexible proximal shaft section, a distal shaft section, and an inflatable cavity filling member on the distal shaft section configured to at least partially fill the body cavity; inserting the catheter through an opening in the patient's skin and advancing the catheter within the patient until the inflatable cavity filling member on the distal shaft section of the catheter is disposed in the body cavity at the intracorporeal location; inflating the inflatable cavity filling member after disposing the inflatable cavity filling member within the body cavity, but before closing the opening, using the flexible proximal shaft section; deploying the flexible proximal shaft section in a folded or coiled configuration within a subcutaneous region of the patient; and closing the opening in the patient's skin so as to prevent pathogen access therethrough.

One embodiment of a catheter device having features of the invention has a proximal shaft section that is flexible enough to be folded, e.g. folded over upon itself, or coiled and placed within a subcutaneous region through an opening in the patient's skin. After deployment of the proximal shaft section of the catheter device, the opening in the patient's skin is closed or sealed, e.g. by sutures, staples or clips adhesives and the like.

In another embodiment of a catheter device having features of the invention has a detachable proximal shaft section or sections to allow the distal shaft section of the catheter device to remain within the patient and sealed therein by closing the access opening in the patient's skin, Additionally, the catheter device and method of using the device may include application of a vacuum within the body cavity that is effective to draw tissue surrounding the body cavity towards the surface of the cavity filling member of the catheter device, which is placed within the body cavity.

A catheter device embodying features of the invention may also include an anti-bacterial agent on or incorporated within a surface of the device to further prevent infection. The catheter device is preferably configured to be deployed within the patient for a period of time from a few days to a few weeks.

The flexible proximal shaft section may be formed of suitable compliant polymers such as polyolefins (e.g. polyethylene and polypropylene), polyurethanes, polyesters, polyvinylchloride, polystyrene, thermoplastic polymers such as C-Flex® (Consolidated Polymer Technologies, Inc., Clearwater Fla. 33762), block polymers such as Kraton™ (Kraton Polymers, Houston Tex. 77208), an ionomer such as Surlyn® (Dupont, Wilmington Del. 19880), nylon, latex rubber, and silicon rubber (e.g., SILASTIC™, Dow Corning, Midland, Mich.).

Body cavities, particularly cavities from which tissue has been removed (e.g. for biopsy) are typically not uniform in size or regular in shape. The catheter devices and systems and methods of using such devices or systems having features of the invention utilize suction to draw tissue surrounding the body cavity against the surface of the cavity filling member on the distal shaft section of the catheter device within a body cavity to ensure good contact therebetween.

DETAILED DESCRIPTION OF EMBODIMENTS

The present invention is directed to catheter devices and methods of using such devices for temporarily maintaining access to an intracorporeal cavity in a targeted tissue region within in a patient's body, such as a biopsy site or a cavity left after removal of a tissue specimen. The catheter device embodying features of the invention has an elongated shaft with a proximal shaft portion that is either detachable or foldable or coilable to facilitate deployment of the proximal end of the catheter within the tissue surrounding the biopsy site. After tissue has been removed from the targeted tissue region, the cavity filling member on the distal end of the catheter is inserted through an opening in the patient's skin and advanced through a passageway in the patient to the body cavity where the cavity filling member is deployed. The proximal shaft section of the catheter is folded or coiled and placed in a subcutaneous location and the opening in the patient's skin is closed or otherwise sealed, e.g. by sutures, staples, clips, adhesive or the like. A vacuum may be applied to cavity to enhance contact between the cavity filling member and the tissue defining the cavity before the opening in the patient's skin in closed or sealed.

Figure 1:
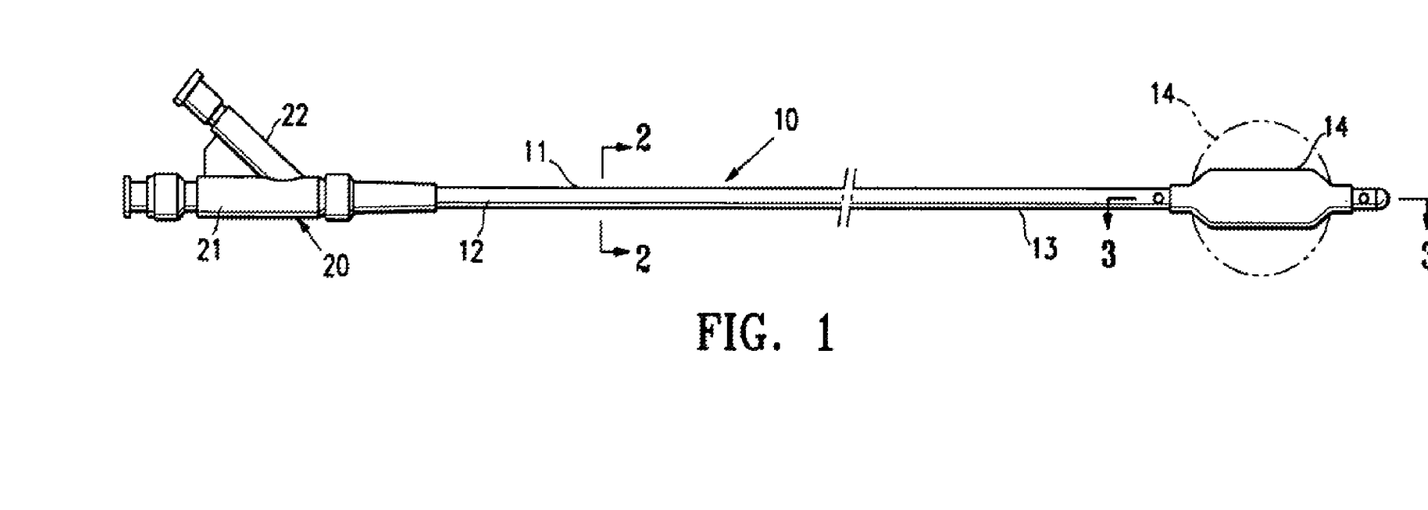
FIG. 1 is a partial elevational view of a catheter device embodying features of the invention which has a balloon configured to temporarily maintain the shape of a cavity in a patient's body tissue.
Figure 2:
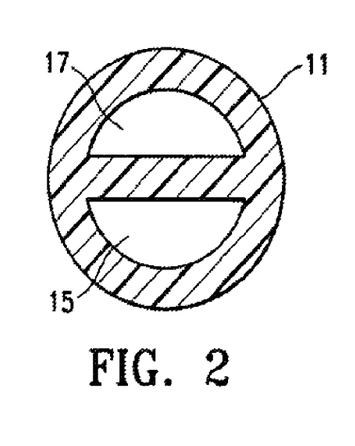
FIG. 2 is a transverse cross-sectional view of the catheter device shown in FIG. 1 taken along line 2-2.
Figure 3:
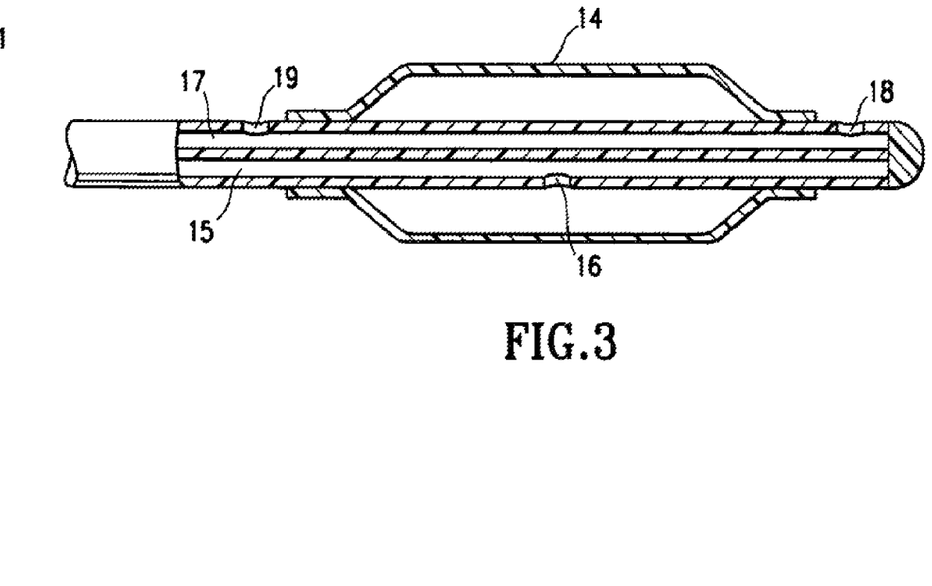
FIG. 3 is an enlarged longitudinal cross section of the distal shaft section of the catheter device shown in FIG. 1 taken along the line 3-3.

FIGS. 1-3 illustrate a catheter device 10 embodying features of the invention which has an elongated shaft 11, a flexible proximal shaft section 12, a distal shaft section 13 and a cavity filling inflatable balloon 14 on the distal shaft section.

As shown in FIGS. 2 and 3, the elongated shaft 11 has an inflation lumen 15 extending from the proximal end of the shaft 11 to a discharge port 16 to discharge inflation fluid within the interior of the balloon 14. The elongated shaft 11 also has a vacuum lumen 17 which extends from the proximal end of shaft 11 to a vacuum port 18 located distal to the balloon 14 and a vacuum port 19 proximal to the balloon 14. Alternatively, individual vacuum lumens may be provided for each vacuum port. Passage of inflation fluid through inflation lumen 15 and discharge port 16 is effective to inflate the balloon 14. Inflation fluid may be a gas or a liquid, and is typically inert. Suitable gases may be air, nitrogen or carbon dioxide. Suitable fluids include water, saline, mineral oil and contrast media with radiopaque material. The balloon in an inflated configuration is shown in phantom in FIG. 1.

Vacuum applied through the one or more vacuum ports 18 and 19 to the body cavity is effective to urge tissue surrounding the cavity into contact with at least a portion of the surface of the outer balloon 14.

The catheter device 10 has a two-arm adapter 20 on the proximal end of the elongated shaft 11. One arm 21 has an inner lumen (not shown) that is in fluid communication with the inflation lumen 15 and the other arm 22 has an inner lumen (not shown) that is in fluid communication with the vacuum lumen 17.

Figures 4, 5, 6:
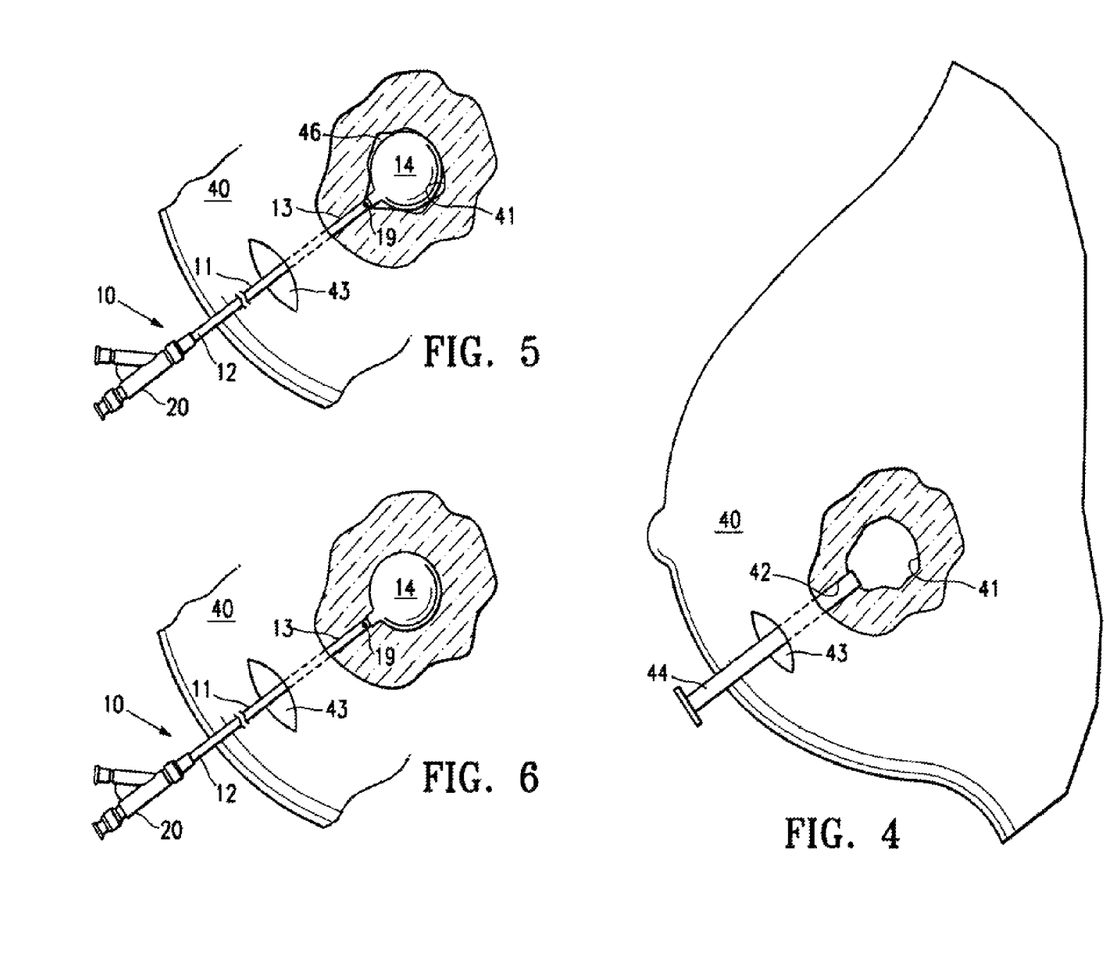
FIG. 4 is an elevational view, partially in section, of a patient's breast after removal of a tissue specimen therefrom.
FIG. 5 is a partial elevational view, partially in section, of a patient's breast device with the catheter shown in FIG. 1 deployed within the patient and the cavity filling balloon inflated within the cavity.
FIG. 6 is a partial elevational view, partially in section, of a patient's breast with the catheter device shown in FIG. 1 deployed within the patient with the cavity filling balloon inflated within the cavity and after the application of a vacuum within the cavity to pull the cavity lining into contact with the inflated cavity filling balloon.

FIG. 4 illustrates a patient's breast 40 which has had a tissue specimen removed, leaving a biopsy cavity 41. An accessing passageway 42 extends from an opening 43 made in the patient's skin to the cavity 41. A cannula 44 remains disposed in the passageway 42 after the biopsy device has been removed.

FIG. 5 illustrates the catheter device shown in FIG. 1 disposed within the patient with the cavity filling balloon 13 inflated within the cavity 41 in the patient's breast FIG. 6 illustrates the body cavity 41 after a vacuum is applied to the cavity so as to conform the tissue of the body cavity 41 to the exterior of the balloon 14.

Figure 7:
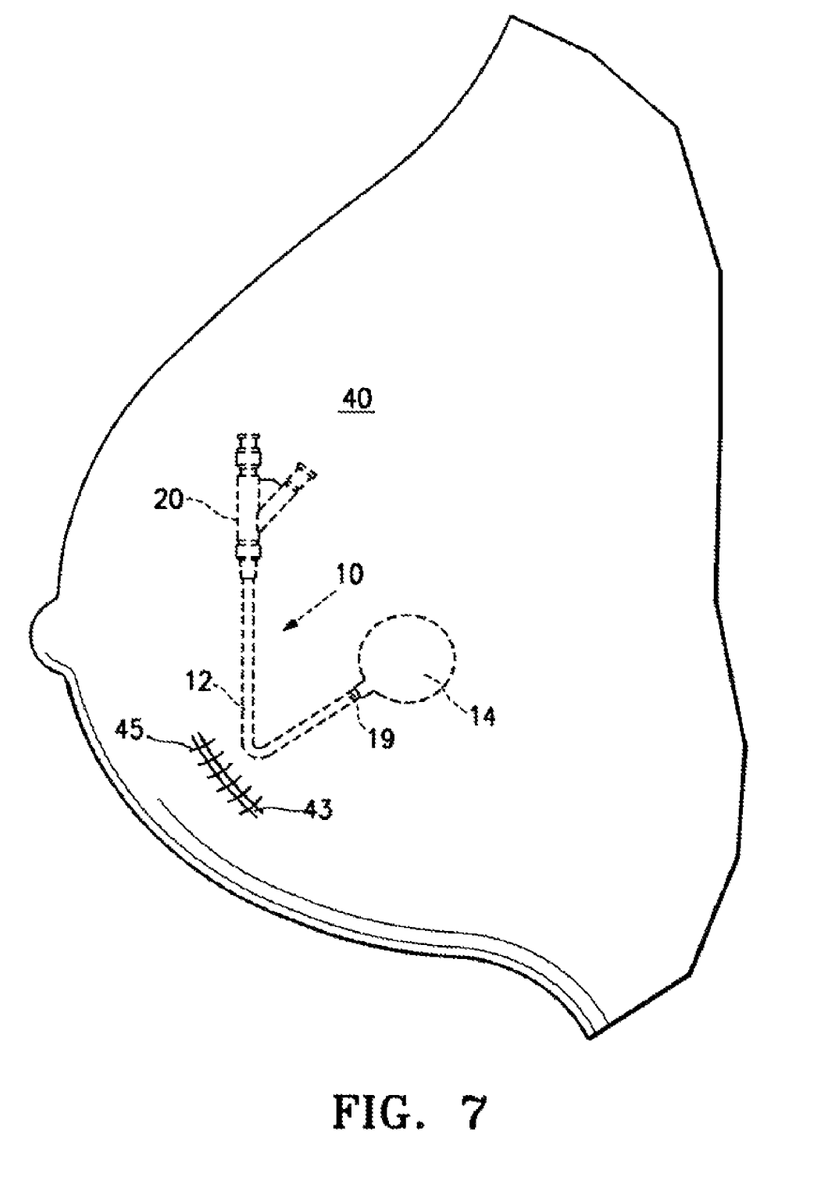
FIG. 7 is an elevational view of a patient's breast with the catheter shown in FIG. 1 completely deployed within the patient and the surgical opening closed.

After the balloon 14 is inflated within the body cavity 41, the flexible proximal shaft section 12 with attached adapter 20 is folded over (or coiled) within the patient's breast 40 and the opening 43 sutured closed with sutures 45. Alternatively, the opening can be closed with a suitable adhesive. A suitable adhesive may also be employed to seal the opening after closure with sutures.

The flexible proximal shaft section 12 can be made flexible enough to be deployed folded or coiled within the patient's breast by thinning the wall of the section or making the wall of a compliant or semi-compliant polymeric material which provides the desired flexibility. Suitable polymeric materials include polyurethane, silicone, C-Flex and Kraton. The proximal shaft section 12 should not have a spring back which would cause discomfort or pain to the patient. The adapter 20 is also preferably formed of flexible materials to facilitate deployment and to minimize pain and discomfort.

The exterior surfaces of the shaft 11 and the balloon 14 are preferably provided with an anti-microbial agent or biocide which retards or prevents pathogen growth within the cavity 41 or the passageway 42. Suitable anti-microbial agents or biocides include silver ions in a hydrophilic carrier, silver ions implanted into the surface of the shaft by ion beam deposition, an antiseptic or disinfectant such as chlorhesqdiene, benzyl chloride. Suitable anti-microbial coatings are provided by Spire, AST, Algon, Surfacine, Ion Fusion and Bacterin International. Other treatment agents such as chemotherapeutic agents may be coated onto or incorporated within the surface of the catheter shaft 11 or balloon 14.

The catheter device 10 which embodies features of the invention is designed to remain within the patient for a few days to several weeks. For example, the catheter device 10 is deployed within the patient's breast after a biopsy specimen has been removed leaving a cavity 41. The catheter device 10 prevents tissue growth within the cavity 41 and the passageway 42. Evaluation of the tissue specimen after removal will determine whether cancer or pre-cancer cells are present or not. If no cancer or pre-cancer cells are found in the specimen, the catheter device may be removed from the patient, the opening re-closed and the catheter device discarded. If cancer cells are found, a radiation balloon catheter such as described in U.S. Pat. No. 6,923,754 to Lubock and U.S. patent application Ser. No. 10/849,410 to Lubock may be utilized to provide radiation treatment to the tissue surrounding the cavity after the temporary catheter device is removed from the patient. The radiation balloon catheter may be advanced through the passageway 42 until the balloon on the catheter is deployed within the cavity 41. The radiation balloon is inflated in a conventional manner so that a uniform dose of radiation is provided to the tissue lining the cavity.

Although a cavity 41 is typically an artificial cavity remaining after removal of tissue at biopsy, surgery, or other medical procedure, a body cavity may be a natural body cavity. For example, devices 10 may be inserted into a bladder for the treatment of bladder cancer. Application of suction is effective to enhance contact with a device 12 in such an example as well. Such enhanced contact may be effective to improve the delivery of radiation or other treatment, and may be effective to avoid "hot spots" (tissue regions receiving more radiation than is received by neighboring tissue regions) and is one of the important advantages provided by the present invention.

Vacuum applied to intermediate space 45 effects good contact between tissue surrounding body cavity 41 and the wall of the balloon 14.

FIGS. 8-11 illustrate a catheter device 50 embodying features of the invention which has an elongated shaft 51, detachable proximal shaft sections 52 and 53, a distal shaft section 54 and a cavity filling inflatable balloon 55 on the distal shaft section. The elongated shaft 51 has an inflation lumen 56 extending from the proximal end of the detachable proximal shaft section 52 to a discharge port 57 in fluid communication with the interior of balloon 55 to discharge inflation fluid therein to inflate the balloon 55. A one-way valve element 60 is disposed within the inflation lumen 56 to allow passage of inflation fluid to the interior of the balloon 55 but prevent discharge of the inflation fluid in the reverse direction. Alternatively or additionally, a one-way valve 61 may also be employed at the discharge port 57 for the same purpose.

The elongated shaft 51 may also has a vacuum lumen 62 which extends from the proximal end of detachable proximal shaft section 53 to a vacuum port 63 located distal to the balloon 55 and a vacuum port 64 proximal to the balloon. A one-way valve 65 may be provided within the vacuum lumen 62 to maintain the vacuum which is developed within the body cavity. While only one vacuum lumen 62 is shown in communication with the vacuum ports 63 and 64, separate vacuum lumens may be provided for each of the vacuum ports.

Figure 8:
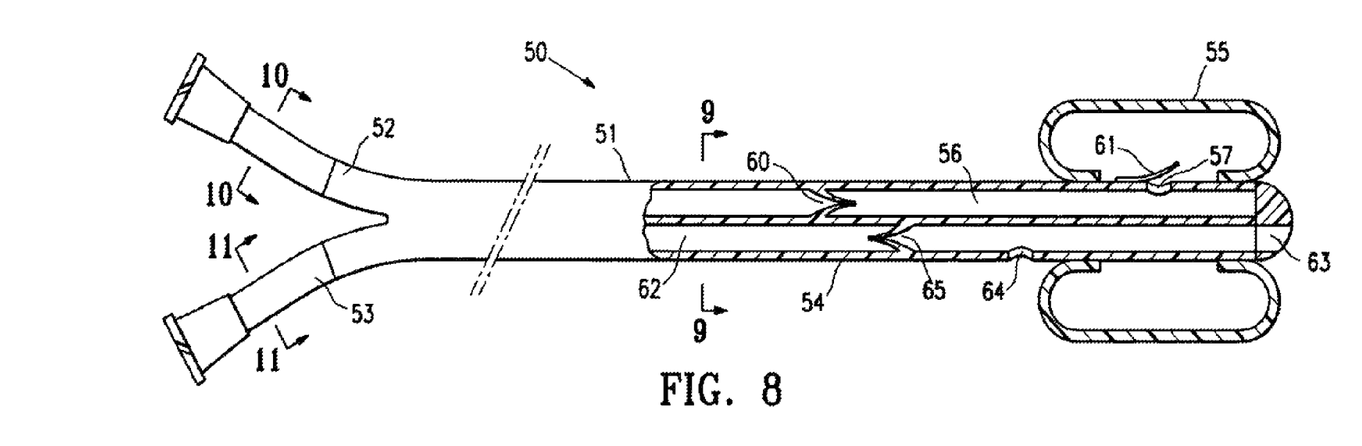
FIG. 8 is an elevational view of a temporary catheter having features of the invention having a detachable proximal portion or portions which can be removed after the distal shaft section has been deployed within the patient.
Figure 9:
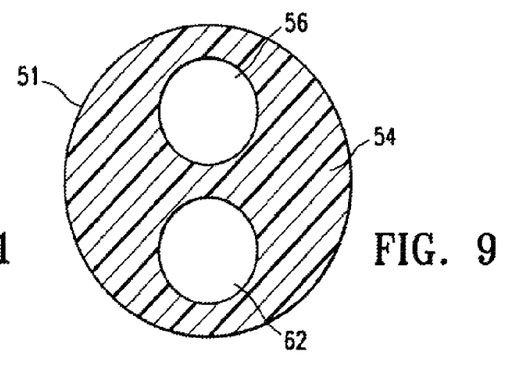
FIG. 9 is a transverse cross-sectional view of the catheter device shown in FIG. 8, taken along the lines 9-9.
Figure 10:
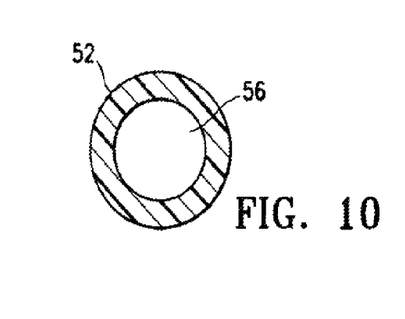
FIG. 10 is a transverse cross-sectional view of the catheter device shown in FIG. 8, taken along the lines 10-10.
Figure 11:
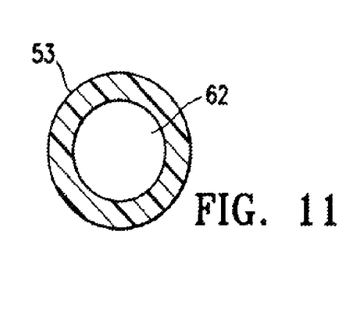
FIG. 11 is a transverse cross-sectional view of the catheter device shown in FIG. 8, taken along the lines 11-11.

The one way valve elements 60 and 65 provided within the inflation and vacuum lumens 56 and 62 respectively may be reed or duckbilled valve elements. The one way valve 61 may be a flapper valve.

The detachable proximal shaft sections 52 and 53 may be connected to the distal shaft section 54 of the catheter device 50 by threaded connections, friction fit connections or other suitable releasable connections. Moreover, while separate detachable proximal shaft sections are shown, they may be combined into a single detachable proximal shaft section.

After a biopsy specimen is removed from the patient, leaving a cavity therein, the catheter device 50 is advanced within the patient until the cavity filling balloon 55 is disposed within the cavity. Inflation fluid is introduced into the interior of the balloon 55 through the inflation lumen 56. The inflation fluid passes through the one-way valve 60 on its way to the balloon interior. Pressure within the lumen distal to the valve 60 and/or the valve structure prevents inflation fluid from passing proximally through the valve. The balloon 55 is inflated to at least partially fill the body cavity within the patient and preferably not to stretch the tissue surrounding the cavity. Vacuum is then pulled through the vacuum ports 64 and 65 to draw the tissue surrounding the cavity towards the balloon 55 to conform the tissue lining to the exterior of the inflated balloon.

Once the balloon 55 is inflated and the vacuum developed to conform the tissue lining to the exterior of the balloon 55, the proximal shaft sections 52 and 53 can be detached from the catheter shaft and the opening in the patient's skin can be closed by suturing, adhesives or other suitable means. The one way valves 60 and/or 61 and 65 minimize or prevent loss of inflation fluid and vacuum.

The portion of the catheter device 50 which remains in the patient can be removed by accessing the proximal portion of the catheter device which remains in the patient by opening the original opening that had been closed or forming a new opening in the patient's skin. The catheter shaft can be severed proximal to the balloon to release the inflation fluid and deflate the balloon to facilitate its withdrawal. If needed, a radiation balloon catheter can be inserted into the patient as previously described to irradiate the tissue lining of the body cavity. If radiation or other treatment is not needed, the opening in the patient's skin may be closed.

While particular forms of the invention have been illustrated and described herein, it will be apparent that various modifications of the invention can be made to the invention. For example, while the various embodiments of the invention have been described herein in terms of a catheter device for treating a biopsy site, it should be apparent that the catheter device and the method of use may be employed elsewhere in the patient's body. Accordingly, it is not intended that the invention be limited to the specific embodiments illustrated.

Terms such as "element", "member", "device", "section", "component", "portion", "means", "step" and words of similar import, when used in the following claims, shall not be construed as invoking the provisions of 35 U.S.C. §112(6) unless the claims expressly use the term "means" followed by a particular function without specific structure or the terms "step" or "steps" followed by a particular function without specific action. All patents and patent applications referred to herein are incorporated by reference in their entirety.

What is claimed is:

1. A method for maintaining access to a biopsy cavity within a patient, comprising:
   providing a temporary catheter having an elongate shaft, a flexible proximal shaft section, and a distal shaft section having an inflatable member thereon;
   inserting the inflatable member on the distal shaft section into the biopsy cavity;
   inflating the inflatable member, after inserting the inflatable member within the biopsy cavity, to at least partially fill the biopsy cavity;
   maintaining the inflated inflatable member in the biopsy cavity for a period of time;
   deflating the inflated inflatable member;
   removing the temporary catheter from the patient;
   inserting a portion of a radiation catheter having an expandable member into the biopsy cavity; and
   expanding the expandable member of the radiation catheter within the biopsy cavity.

2. The method of claim 1, further comprising conforming tissue adjacent the biopsy cavity to an exterior of the inflatable member.

3. The method of claim 2, wherein the conforming is via application of a vacuum.

4. The method of claim 1, wherein the expandable member is a balloon.

5. The method of claim 1, wherein the temporary catheter is removed from the patient after a period of about 2 days to several weeks.

6. The method of claim 1, wherein the inflatable member is an inflatable balloon.

7. The method of claim 1, wherein the inflatable member is deflated to remove the temporary catheter from the patient.

8. A method of temporarily filling an intracorporeal site within a breast of a patient, comprising:
   forming a cavity at a desired intracorporeal location in the breast;
   forming a passageway in the breast to the desired intracorporeal location;
   providing a catheter device having an elongated shaft with a flexible proximal shaft section, a distal shaft section and a cavity filling member on the distal shaft section;
   advancing the catheter device through the passageway until the cavity filling member on the distal shaft section is disposed within the cavity formed in the breast;
   expanding the cavity filling member after disposing the cavity filling member within the cavity in the breast to at least partially fill the cavity;
   contracting the expanded cavity filling member;
   inserting a portion of radiation catheter having an expandable member into the patient through the passageway; and
   expanding the expandable member on the radiation catheter within the biopsy cavity.

9. The method of claim 8, further comprising conforming tissue adjacent the cavity to an exterior of the cavity filling member.

10. The method of claim 9, wherein the conforming is via application of a vacuum.

11. The method of claim 8, wherein the radiation catheter is a radiation balloon catheter and the expandable member is a balloon.

12. The method of claim 8, wherein the catheter device is removed from the patient after a period of about 2 days to several weeks.

13. The method of claim 8, wherein the cavity filling member is an inflatable balloon.

14. The method of claim 8, wherein the cavity filling member is deflated to remove the catheter device from the patient.

15. A method for maintaining access to a body cavity at an intracorporeal location of a patient, comprising:
   providing a catheter having an elongate shaft, a flexible proximal shaft section, a distal shaft section, and an inflatable cavity filling member on the distal shaft section;
   forming a passageway to the intracorporeal location;
   advancing the catheter through the passageway in the patient until the inflatable cavity filling member on the distal shaft section of the catheter is disposed in the body cavity at the intracorporeal location;

inflating the inflatable cavity filling member after disposing the inflatable cavity filling member within the body cavity to at least partially fill the body cavity;

deflating the inflated inflatable cavity filling member;

inserting a portion of a radiation catheter having an expandable member into the body cavity through the passageway; and expanding the expandable member of the radiation catheter within the body cavity.

16. The method of claim 15, further comprising conforming tissue adjacent the body cavity to an exterior of the inflatable cavity filling member.

17. The method of claim 15, wherein the passageway is formed at an opening in the patient's skin to the intracorporeal location.

18. The method of claim 17, wherein tissue is removed from the intracorporeal location to form the body cavity.

19. The method of claim 15, wherein the radiation catheter is a radiation balloon catheter and the expandable member is a balloon.

* * * * *